(12) United States Patent
Mori et al.

(10) Patent No.: US 6,348,479 B1
(45) Date of Patent: Feb. 19, 2002

(54) WATER-IN-OIL EMULSIFIER COMPOSITION

(75) Inventors: Michio Mori, Higashiosaka; Tsuguo Yabuta, Ibaraki; Osamu Matsuoka, Yokohama, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/554,071

(22) PCT Filed: Nov. 6, 1998

(86) PCT No.: PCT/JP98/04998

§ 371 Date: May 11, 2000

§ 102(e) Date: May 11, 2000

(87) PCT Pub. No.: WO99/25310

PCT Pub. Date: May 27, 2000

(30) Foreign Application Priority Data

Nov. 14, 1997 (JP) ............................................. 9-312533

(51) Int. Cl.⁷ .................... A61K 9/107; A61K 31/4402; B01F 17/34
(52) U.S. Cl. .................... 514/357; 424/78.05; 514/846; 514/887; 514/944; 516/29; 516/902; 516/918
(58) Field of Search .......................... 516/29, 902, 918; 424/78.05; 514/846, 887, 944, 357

(56) References Cited

U.S. PATENT DOCUMENTS

| | | | | |
|---|---|---|---|---|
| 3,936,391 A | * | 2/1976 | Gabby et al. ............ | 516/918 X |
| 4,244,942 A | * | 1/1981 | Kamashita et al. .. | 424/78.05 X |
| 4,690,774 A | * | 9/1987 | Vishnupad et al. ............ | 516/29 |
| 4,950,475 A | * | 8/1990 | Vishnupad et al. ..... | 514/944 X |
| 5,000,937 A | * | 3/1991 | Grollier et al. ......... | 514/944 X |
| 5,362,482 A | * | 11/1994 | Yoneyama et al. ..... | 514/846 X |
| 5,424,469 A | * | 6/1995 | Jakobson et al. ............ | 554/227 |
| 5,429,816 A | * | 7/1995 | Hofrichter et al. ...... | 514/944 X |

* cited by examiner

Primary Examiner—Richard D. Lovering
(74) Attorney, Agent, or Firm—Oblon, Spivak, McClelland, Maier & Neustadt, P.C.

(57) ABSTRACT

This invention provides a milk lotion, cream or the like which does not undergo oil-water phase separation but remains stable for a long time and, in addition, has a good skin feel with good spreadability. It is a water-in-oil emulsifier composition comprising liquid oil basis, liquid oil component gelling agent, water and, as a water-in-oil type surfactant, polyglycerin fatty acid ester and/or polyoxyethylene hydrogenated castor oil.

6 Claims, No Drawings

WATER-IN-OIL EMULSIFIER COMPOSITION

This application is a 371 of PCT/JP98/04998, filed Nov. 6, 1998.

TECHNICAL FIELD

This invention relates to a water-in-oil emulsion and more particularly to a water-in-oil emulsion which finds application in cosmetic products, quasi-drugs and other fields and which does not separate into water and oil phases but remains stable and provides a good skin feel.

BACKGROUND ART

As the emulsions in use as a cosmetic products and quasi-drugs, O/W (oil-in-water) milk lotions and creams or W/O (water-in-oil) milk lotions and creams are known.

O/W milk lotions and creams are satisfactory in the stability and feel of the system but rather poor in skin barrier property and absorbability of active ingredients. On the other hand, W/O milk lotions and creams are antithetical to said O/W milk lotions and creams in that while the former are satisfactory in skin barrier property and absorbability of active ingredients, they have the disadvantage that the system is unstable and liable to separate into aqueous and oil phases. Prevention of water-oil phase separation can be achieved by increasing the formulating amount of a solid oil basis but the practice aggravates the skin feel due to the stickiness and poor spreadability on the skin.

DISCLOSURE OF INVENTION

The inventors of this invention found that a water-in-oil emulsion improved in the above problematic attributes can be obtained by adding a liquid oil component gelling agent to a liquid oil basis to gelatinize the latter and mix-emulsifying it with water gelatinized with a specific water-in-oil type surfactant in advance.

The water-in-oil emulsion of this invention comprises liquid oil basis, liquid oil component gelling agent, water, and water-in-oil type surfactant which is polyglycerin fatty acid ester and/or polyethylene hydrogenated castor oil.

The water-in-oil emulsion of this invention includes milk lotions and creams, among others.

The liquid oil basis for use in this invention is an oil basis which is liquid at ambient temperature and, as such, includes but is not limited to fatty acid esters (e.g. cetyl isooctanoate, hexyl laurate, decyl oleate, methyl polysiloxane, cetyl octanoate, isopropyl myristate, isocetyl myristate, etc.), liquid paraffin, olive oil, tsubaki oil, rapeseed oil, 2-octyldodecanol, squalane, squalene, oleic acid and so on. These liquid oil bases can be used independently or in a combination of two or more species.

The formulating amount of the liquid oil basis in the composition of this invention is 5~30%, preferably 10~25%, by weight.

The liquid oil component gelling agent as used in this invention is intended to gelatinize said liquid oil basis and other optionally formulated oily component inclusive of the active ingredient, and includes, among others, aluminum hydroxide, 12-hydroxystearic acid, carnauba wax, microcrystalline wax, and straight-chain higher saturated fatty acid esters of dextrin (e.g. dextrin palmitate, dextrin stearate, dextrin behenate, dextrin myristate, dextrin cocofatty acid ester, dextrin laurate, etc.). Among these esters, dextrin palmitate is preferred.

The formulating amount of said gelling agent in the composition of this invention is 0.5~15%, preferably 1~10%, by weight.

Water for use in this invention may for example be purified water, distilled-water or tap water.

The proportion of water in the composition of this invention is 30~80%, preferably 40~70%, by weight. To insure a further improvement in skin feel, the formulating amount of water in the composition of this invention is preferably larger, particularly not less than twice larger, than the formulating amount of said oil component inclusive of said liquid oil basis.

The water-in-oil type surfactant to be used for gelling said water in this invention includes polyoxyethylene hydrogenated castor oil (e.g. polyoxyethylene (3)-hydrogenated castor oil, polyoxyethylene (5)-hydrogenated castor oil, polyoxyethylene (7)-hydrogenated castor oil, polyoxyethylene (10)-hydrogenated castor oil, etc.), polyglycerin fatty acid esters (e.g. polyglycerin condensed ricinoleate, polyglycerin stearate, polyglycerin oleate, etc.). With other kinds of water-in-oil type surfactants, the objective emulsifier composition which is stable and has a good skin feel cannot be obtained.

These water-in-oil type surfactants can be used independently or in a combination of two or more species.

The formulating amount of the water-in-oil type surfactant in the composition of this invention is 0.5~15%, preferably 1~10%, by weight.

Preferably the composition of this invention further contains one or more active ingredients. The active ingredients which can be incorporated include, among others, antipruritic agents such as diphenhydramine, diphenhydramine hydrochloride, diphenhydramine salicylate, crotamiton, chlorpheniramine maleate, etc., antiinflammatory agents such as glycyrrhetinic acid, dipotassium glycyrrhetinate, and emolients such as urea, sodium hyaluronate, and glycerin.

When a liquid oily drug (e.g. diphenhydramine, crotamiton, etc.) is to be formulated in a large amount, the formulating amount of said liquid oil basis may be reduced to bring the total amount of the liquid oil basis and oily drug into the above-mentioned formulation range.

The composition of this invention may be further supplemented with the conventional buffer (e.g. potassium dihydrogenphosphate, anhydrous sodium monohydrogenphosphate, etc.), a flavoring agent (e.g. 1-menthol etc.), an emulsifier stabilizer (eg. an inorganic salt such as magnesium sulfate), and an antiseptic (e.g. methyl p-hydroxybenzoate, propyl p-hydroxybenzoate, etc.).

The composition of this invention is produced as follows. On the one hand, said liquid oil component gelling agent, water-in-oil type surfactant, optionally liquid oily drug, flavoring agent, etc. to said liquid oil basis and the mixture is warmed for dissolution to give a homogeneous solution (A).

On the other hand, optionally said active ingredient (e.g. urea), buffer, antiseptic etc. are added to water and warmed for dissolution to give a homogeneous solution (B).

To the above solution (A) is added the above aqueous solution (B), and the mixture is stirred for emulsification, followed by cooling to ambient temperature.

EFFECT OF INVENTION

Stability Test

The milk lotions obtained in Examples 1~4 and Comparative Examples 1~5, presented hereinafter and summarized in Table 2, were respectively examined grossly for the appearance immediately after preparation. The lotions were stored in a constant-temperature room at 40° C. or 50° C. and examined for the appearance after 6 months or 3 months, as the case may be, and evaluated according to the following criteria.

Water-oil phase separation:

| | |
|---|---|
| None | : ○ |
| Slight | : Δ |
| Definite | : x |

Sensory test

In a panel consisting of 15 men and women from 30 to 75 years of age, a sensory test was performed for spreadability and stickiness on the skin.

| Evaluation criteria | | Score |
|---|---|---|
| Spreadability on skin | Good: | 3 points |
| | Slightly poor: | 2 points |
| | Poor: | 1 point |
| Stickiness | None: | 3 points |
| | Slight: | 2 points |
| | Sticky: | 1 point |

Based on the sum of scores for n=15 for each attribute, the test result was expressed as follows.

Spreadability on skin:
≧40 points: ○
30~<40 points: Δ
<30 points: x

Tackiness on skin:
≧40 points: ○
30~<40 points: Δ
<30 points: x

The results are shown in Table 1.

TABLE 1

| | Example | | | | Comparative Example | | | | |
|---|---|---|---|---|---|---|---|---|---|
| | 1 | 2 | 3 | 4 | 1 | 2 | 3 | 4 | 5 |
| Stability test | | | | | | | | | |
| Immediately after production | ○ | ○ | ○ | ○ | ○ | ○ | ○ | ○ | ○ |
| 40° C., 6 months | ○ | ○ | ○ | ○ | x | x | x | x | ○ |
| 50° C., 3 months | ○ | ○ | ○ | ○ | x | x | x | x | Δ |
| Sensory test | | | | | | | | | |
| Spreadability on skin | ○ | ○ | ○ | ○ | Δ | Δ | Δ | ○ | x |
| Tackiness on skin | ○ | ○ | ○ | ○ | ○ | ○ | ○ | ○ | x |

It will be apparent from Table 1 that the composition of this invention does not separate into aqueous and oil phases but remains stable for a long time after production and that the composition is very satisfactory in skin feel as well.

TABLE 2

| | Example | | | | Comparative Example | | | | |
|---|---|---|---|---|---|---|---|---|---|
| Recipe (wt. %) | 1 | 2 | 3 | 4 | 1 | 2 | 3 | 4 | 5 |
| W/O surfactant | | | | | | | | | |
| Polyglycerin condensed ricinoleate | 6 | | | | | | 6 | | |
| Polyglycerin stearate | | 6 | | | | | | | |
| Polyglycerin oleate | | | 6 | | | | | | |
| Polyoxyethylene (5) hydrogenated caster oil | | | | 6 | | | | | |
| Polyoxyethylene (6) sorbitan monoleate | | | | | 6 | | | | |
| Polyoxyethylene (2) cetyl ether | | | | | | 6 | | | 11 |
| Polyoxyethylene (2) monooleate | | | | | | | | 6 | |
| Glycerin monostearate | | | | | | | | | 3 |
| Liquid oil | | | | | | | | | |
| Cetyl octanoate | 16 | 16 | 16 | 16 | 16 | 16 | 16 | 16 | |
| Isopropyl myristate | 3 | 3 | 3 | 3 | 3 | 3 | 3 | 3 | |
| Liquid paraffin | | | | | | | | | 28 |
| Solid oil basis | | | | | | | | | |
| Petrolatum | | | | | | | | | 11 |
| Beeswax | | | | | | | | | 6 |
| Oil component gelling agent | | | | | | | | | |
| Dextrin palmitate | 6 | 6 | 6 | 6 | 6 | 6 | 6 | | |
| Propylene glycol | | | | | | | | | 10 |
| Magnesium sulfate | 1 | 1 | 1 | 1 | 1 | 1 | 1 | 1 | 1 |
| Methyl p-hydroxybenzoate | 0.1 | 0.1 | 0.1 | 0.1 | 0.1 | 0.1 | 0.1 | 0.1 | 0.1 |
| Purified water | q.s. | q.s. | q.s. | q.s. | q.s. | q.s. | q.s. | q.s. | q.s. |

EXAMPLES

Example 1

To a mixture of cetyl octanoate (16 g) and isopropyl myristate (3 g), dextrin palmitate (6 g) and polyglycerin condensed ricinoleate acid ester (6 g) were added and dissolved by warming at 80° C. to provide a homogeneous solution (A).

On the other hand, magnesium sulfate (1 g) and methyl p-hydroxybenzoate (0.1 g) were added to purified water (67.9 g) and dissolved by warming at 80° C. to provide a homogeneous solution (B).

To (A) was added (B), and the mixture was emulsified by stirring and, then, cooled to ambient temperature to provide a milk lotion (100 g).

Example 2~4

Three kinds of milk lotions varying in W/O surfactant species as shown in Table 2 were produced in the same manner as in Example 1.

Example 5

To a mixture of cetyl octanoate (16 g) and isopropyl myristate (3 g), diphenhydramine (1 g), crotamiton (5 g), glycyrrhetinic acid (0.3 g), dextrin palmitate (5 g) and polyoxyethylene (5)-hydrogenated castor oil (5 g) were added and dissolved by warming at 80° C. to give a homogeneous solution (A).

On the other hand, urea (10 g), ammonium chloride (1 g) and methyl p-hydroxybenzoate (0.1 g) were added to purified water (53.6 g) and dissolved by warming at 80° C. to give a homogeneous solution (B).

To (A) was added (B), and the mixture was emulsified by stirring and, then, cooled to ambient temperature to provide a milk lotion (100 g).

Example 6

To cetyl octanoate (5 g), diphenhydramine (1 g) crotamiton (5 g), glycyrrhetinic acid (0.3 g), dextrin palmitate (5 g) and polyglycerin condensed ricinoleate (5 g) were added and dissolved by warming at 80° C. to give a homogeneous solution (A).

On the other hand, urea (10 g), ammonium chloride (1 g) and methyl p-hydroxybenzoate (0.1 g) were added to purified water (67.6 g) and dissolved by warming at 80° C. to give a homogeneous solution (B).

To (A) was added (B), and the mixture was emulsified by mixing and, then, cooled to ambient temperature to provide a cream (100 g).

The active ingredient—containing milk lotions and cream thus obtained were as good as the milk lotions obtained in Example 1~4, not showing oil-water phase separation even after 6 months at 40° C. or 3 months at 50° C. and having a satisfactory skin feel with good spreadability on the skin and freedom from tackiness.

Comparative Examples 1~5

Five milk lotions, 100 g each, which varied in the recipe as shown in Table 2 were produced in the same manner as in Example 1.

INDUSTRIAL APPLICABILITY

The water-in-oil emulsion of this invention does not separate into aqueous and oil phases but remain stable for a long time and provides a satisfactory skin feel with good spreadability and freedom from stickiness, thus being suited for use in the field of cosmetic products and quasi-drugs.

What is claimed is:

1. A water-in-oil emulsion comprising liquid oil basis, liquid oil component gelling agent, water, and, as a water-in-oil type surfactant, polyglycerin fatty acid ester and/or polyoxyethylene hydrogenated castor oil, wherein the liquid oil component gelling agent is aluminum hydroxide, 12-hydroxystearic acid, or a dextrin straight-chain higher saturated fatty acid ester.

2. A water-in-oil emulsion as claimed in claim 1 which is a milk lotion or a cream.

3. A water-in-oil emulsion as claimed in claim 1 wherein the dextrin straight-chain higher saturated fatty acid ester is dextrin palmitate.

4. A water-in-oil emulsion as claimed in claim 1 wherein the polyglycerin fatty acid ester is polyglycerin stearate, polyglycerin oleate, or polyglycerin condensed ricinoleate.

5. A water-in-oil emulsion as claimed in claim 1, which further comprises an active ingredient.

6. A water-in-oil emulsion as claimed in claim 5 which comprises at least one member selected from the group consisting of diphenhydramine, diphenhydramine, hydrochloride, diphenhydramine salicylate, crotamiton, chlorpheniramine maleate, glycyrrhetinic acid, dipotassium glycyrrhetinate, urea, sodium hyaluronate, and glycerin as the active ingredient.

* * * * *

UNITED STATES PATENT AND TRADEMARK OFFICE
CERTIFICATE OF CORRECTION

PATENT NO. : 6,348,479 B1  Page 1 of 1
DATED : February 19, 2002
INVENTOR(S) : Mori et al.

It is certified that error appears in the above-identified patent and that said Letters Patent is hereby corrected as shown below:

<u>Title page,</u>
Item [87], PCT Publication information should read:

-- [87]  PCT Pub. No.:   WO99/25310
         PCT Pub. Date:  May 27, 1999 --

Signed and Sealed this

First Day of June, 2004

JON W. DUDAS
*Acting Director of the United States Patent and Trademark Office*